United States Patent [19]
Besserman

[11] 4,284,847
[45] Aug. 18, 1981

[54] AUDIOMETRIC TESTING, ANALYZING, AND RECORDING APPARATUS AND METHOD

[76] Inventor: Richard Besserman, Scottsdale, Ariz.

[21] Appl. No.: 119,818

[22] Filed: Feb. 8, 1980

Related U.S. Application Data

[63] Continuation of Ser. No. 920,684, Jun. 30, 1978, abandoned.

[51] Int. Cl.³ .................................................. H04R 29/00
[52] U.S. Cl. ..................................... 179/1 N; 128/746
[58] Field of Search ................. 179/1 N, 107; 128/746

[56] References Cited
U.S. PATENT DOCUMENTS

| | | | |
|---|---|---|---|
| 3,808,354 | 4/1974 | Feezor et al. ........................ | 179/1 N |
| 3,809,811 | 5/1974 | De Lisle et al. ..................... | 179/1 N |

OTHER PUBLICATIONS

D. McClure, "Hear Ye", IEEE Spectrum, Mar. 1978, p. 34.

*Primary Examiner*—Mark E. Nusbaum
*Assistant Examiner*—E. S. Kemeny
*Attorney, Agent, or Firm*—Cahill, Sutton and Thomas

[57] ABSTRACT

An audiometric testing system containing a processor and programmable analog circuitry for controlling frequency and intensity of audiometric test tones communicates with a remote data processing system via a communications link. The remote data processing system stores prior audiometric records for a large number of subjects. Each day, the audiometric records of a number of selected persons are transmitted from the remote data processing system to a memory of the audiometric testing system in response to identification numbers entered by an operator. The audiometric responses of each person to patterns of sounds of varying frequencies and intensities are determined. The varying frequencies and intensities are determined by a bracketing subroutine of an algorithm stored in and executed by a processor of the audiometric testing system. A person's responses to such test tones are utilized by the bracketing subroutine to determine his threshold levels at the respective frequencies for each ear. The algorithm automatically computes the pure tone averages for each ear from the threshold levels at a plurality of predetermined frequencies. The algorithm also automatically computes the binaural hearing impairment based on test results from prior testing of the person. Any significant shift in threshold is determined by comparison with the prior test results. The audiometric testing system includes a printer which prints the persons' complete hearing test record, including relevant identifying information, present test results, pure tone averages, binaural hearing impairment, significant threshold shifts, and a recommended time for the next testing. After all persons have been tested for the day, their updated audiometric records are transmitted via the communications link to the remote data processing system.

23 Claims, 12 Drawing Figures

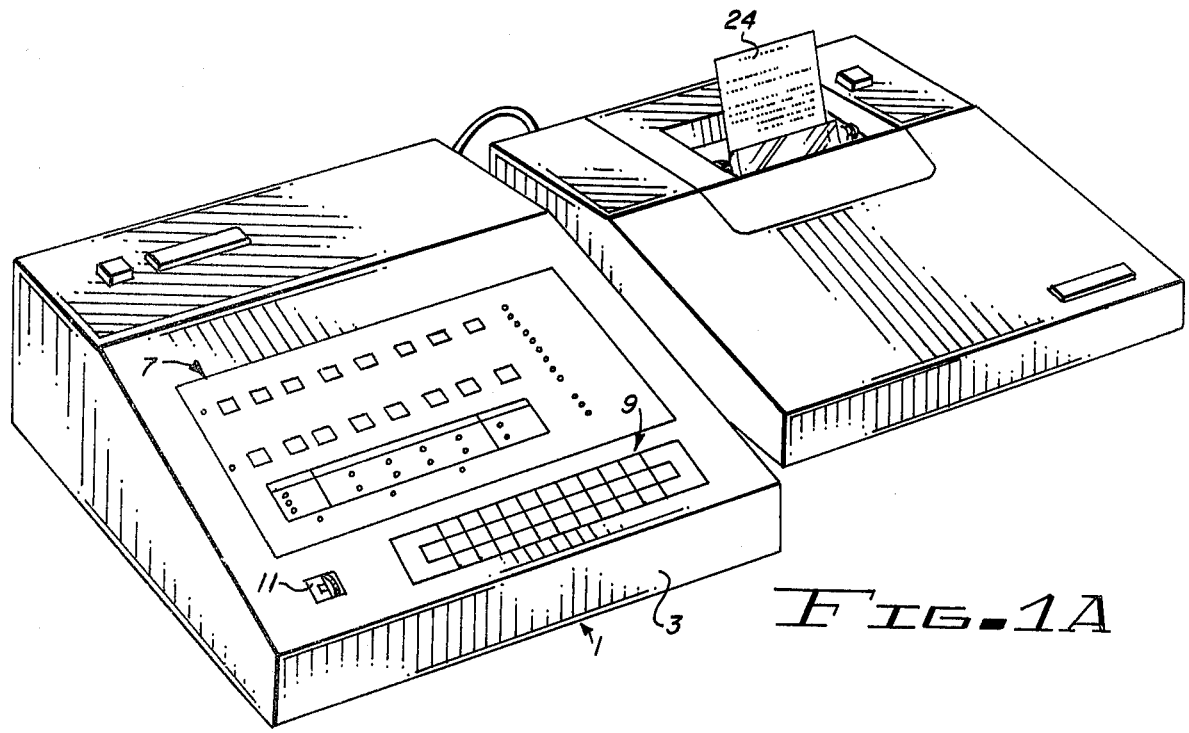
FIG.-1A
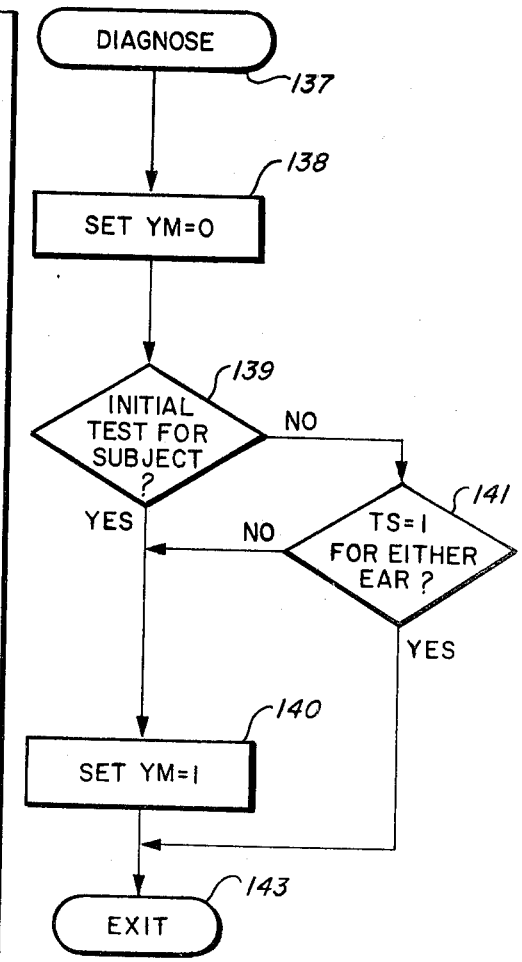
FIG.-2
FIG.-10

FIG. 1B

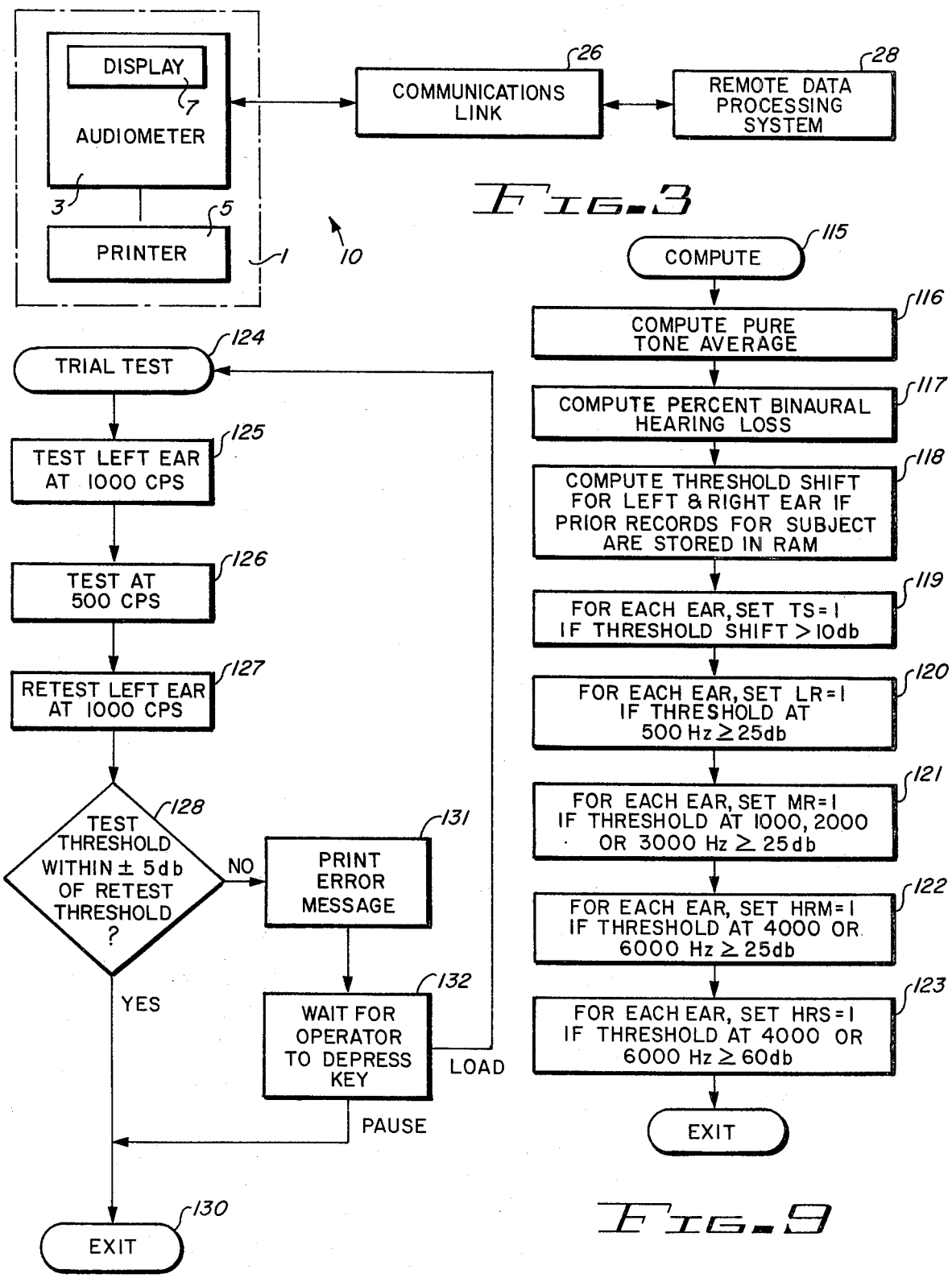

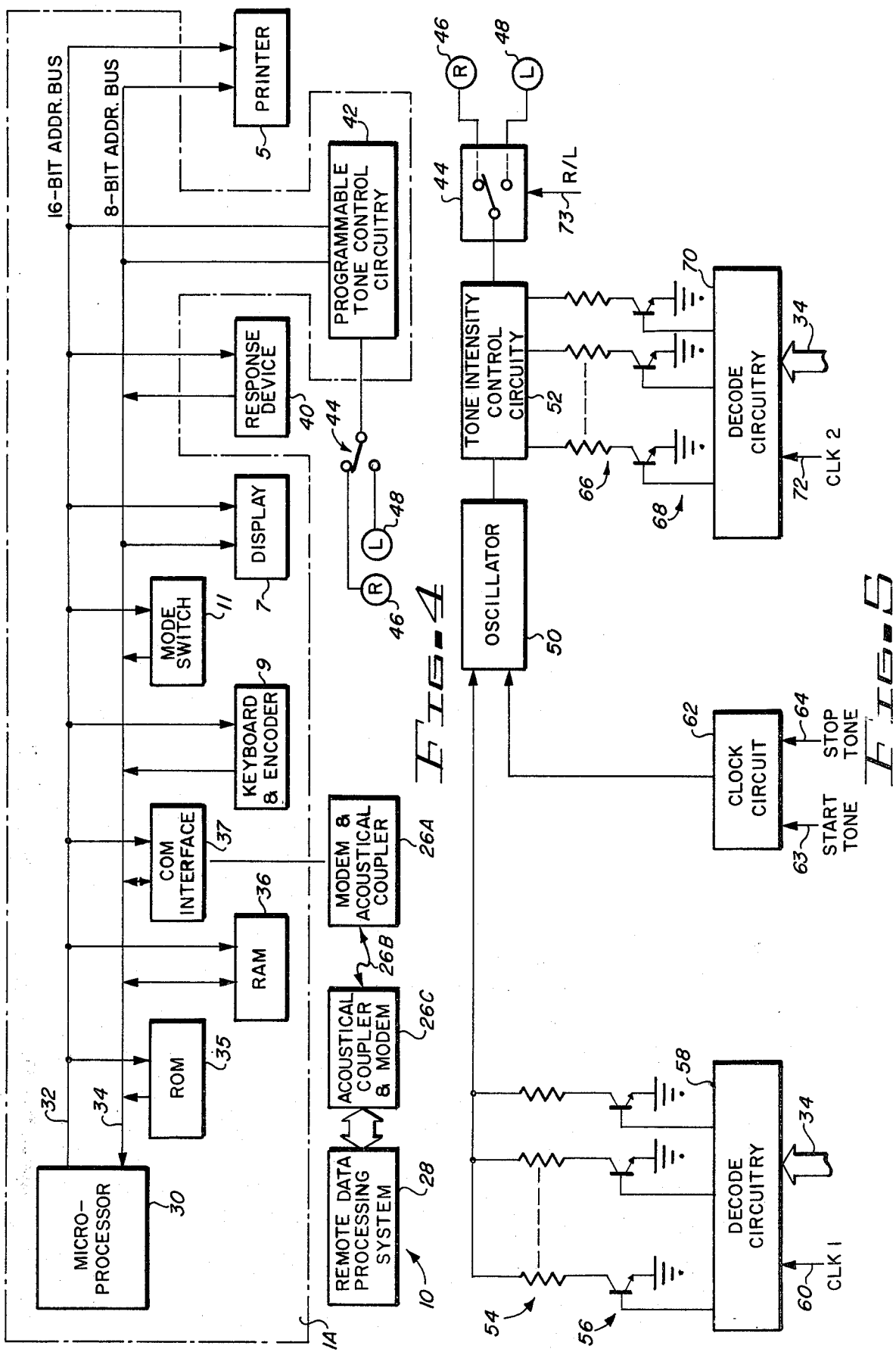

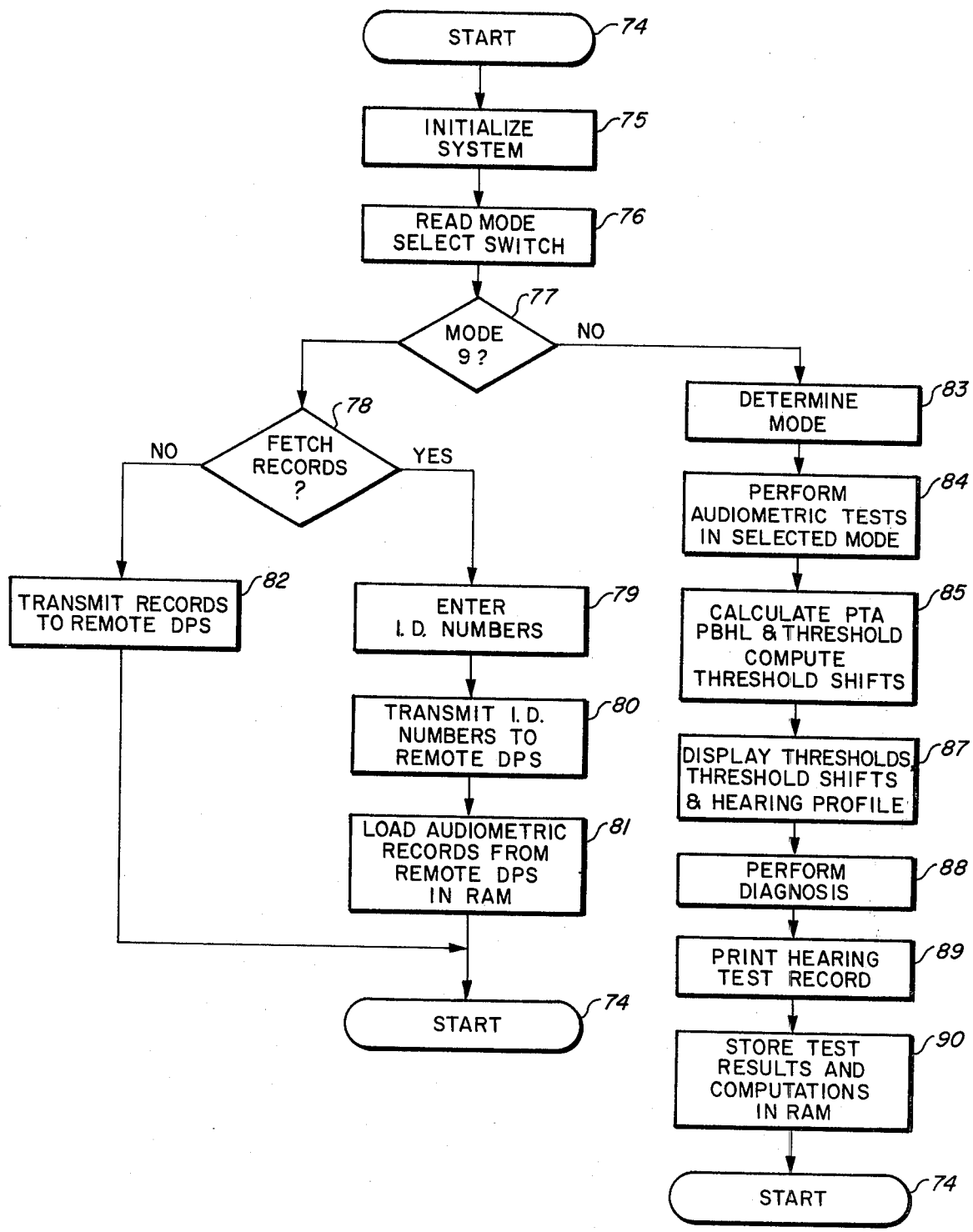
FIG_6

AUDIOMETRIC TESTING, ANALYZING, AND RECORDING APPARATUS AND METHOD

This is a continuation of application Ser. No. 920,684 filed June 30, 1978, now abandoned.

BACKGROUND OF THE INVENTION

1. Field of the Invention:

The invention relates to audiometric testing systems and methods.

2. Description of the Prior Art:

Manufacturing organizations are frequently confronted by problems relating to the harmful effects of industrial noise on hearing of employees. Such companies are subject to liability for hearing damage which can be shown to have been caused by industrial noise levels. Well-being of employees requires that the effects of industrial noise on individual employees be periodically monitored to identify employees who experience hearing threshold shifts. It is further necessary to identify manufacturing areas which produce a sufficiently high noise level to induce hearing threshold shifts in employees. It is also important for manufacturing organizations to be able to provide legally admissible evidence to demonstrate that hearing threshold shifts may have occurred for reasons other than presence of industrial noise.

Various audiometric testing techniques are well known. Some known audiometric testing techniques are described in "Audiometry: Principles and Practices", by Aaron Glorig, M.D., Williams & Wilkons Co., Baltimore, Maryland, 1965. Various threshold bracketing techniques are commonly utilized to determine a person's (hereinafter referred to as a test subject, or simply subject) hearing threshold (hereinafter referred to simply as "threshold" or "threshold level") at various frequencies by incrementing or decrementing the intensity of a test tone applied to one of the subject's ears until he or she satisfactorily indicates that he or she has heard the test tone. A quantity known as the "pure tone average" is commonly computed by averaging the subject's threshold at three frequencies, such as 500, 1,000, and 2,000 cycles per second. Another standard calculation is the percent binaural impairment, which indicates deviation from average or standard hearing levels.

Various audiometers are known, including manual audiometers and automatic audiometers. The most complex prior audiometers automatically produce test tones of varying intensities at various frequencies in response to response signals from the person being tested to bracket the threshold levels of the subject. The state of the art is generally shown by U.S. Pat. Nos. 3,974,335; 3,392,241; 3,808,354; 3,809,811 and 3,810,316. None of the known audiometers operates either as an automatic audiometer or as a manual audiometer, and none of the known audiometers calculates audiometric parameters such as pure tone average and/or percent binaural hearing impairment. Known audiometers do not compare the subject's present test results with his previous test results. In summary, there is a presently unmet need for a low-cost system and method for performing audiometric testing and associated bookkeeping tasks to enable manufacturing employers to economically implement necessary hearing conservation programs.

SUMMARY OF THE INVENTION

Accordingly, it is an object of the invention to provide an economical audiometric test system and technique for implementing hearing conservation programs.

It is another object of the invention to provide an audiometric test system which is capable of either automatic or manual operation.

It is another object of the invention to provide an audiometric test system capable of accessing a remote data base to retrieve a group of audiometric records for a corresponding group of test subjects.

It is another object of the invention to provide an audiometric test system which automatically performs audiometric parameter caculations and stores the computed audiometric parameter values.

It is another object of the invention to provide an audiometric test system and method for producing original documents containing the audiometric history of a patient or test subject.

It is another object of the invention to provide an audiometric test system and method which automatically instructs an operator to operate the audiometric test system.

It is another object of the invention to provide an audiometric test system which minimizes the amount of required keyboard entry of information.

Briefly described, and in accordance with one embodiment thereof, the invention provides an audiometric test system and method for testing a test subject's (hereinafter, simply "subject") hearing to determine threshold levels at various frequencies, automatically computing audiometric parameters from such threshold levels, automatically determining the presence of any significant threshold level shifts of the subject by comparing the subject's present test results with the prior test results, and automatically indicating the presence of any significant threshold level shifts. In one embodiment of the invention the audiometric parameters computed include the pure tone average and binaural hearing impairment for each ear. In another embodiment of the invention, the audiometric system includes a processor including a memory for storing an operating algorithm and a random access memory for storing audiometric records for a plurality of persons. Audiometric test tones are produced by programmable analog circuitry including programmable oscillators for determining test tone frequencies and programmable attenuators responsive to signals produced by the programmable oscillators. In one embodiment of the invention, a printer is operatively connected to the processor for printing out updated audiometric records of a selected subject. The present test results are stored in the random access memory, updating the audiometric records of the subject. In one embodiment of the invention, the printout includes diagnostic information, including information confirming a threshold level shift detected at a previous testing session and/or recommending subsequent audiometric testing dates and/or treatment. In another embodiment of the invention, a communications link operatively couples the processor to a remote data processing system storing a large number of audiometric records containing prior test results for different subjects. A selected group of such audiometric records can be retrieved by accessing the remote data processing system via the communications link and loading the "fetched" audiometric records in the random access memory. The individual subject's audiometric responses are then individually tested. In another embodiment of the invention, identifying information, past test results, and audiometric history information fetched from the remote data processing system or entered via a keyboard of the audiometric test system are printed by means of the printer. After a predetermined number of subjects have been tested, updated and/or new audiometric records are transmitted from the memory to the remote data processing system via the communications link.

BRIEF DESCRIPTION OF THE DRAWINGS

FIG. 1A is a perspective view of the audiometer and associated printer according to the invention.

FIG. 1B is an enlarged view of the display of FIG. 1A.

FIG. 2 shows a sample "print out" of the printer of FIG. 1A.

FIG. 3 is a block diagram illustrating connection of the audiometer and printer to a remote data processing system via a telephone communications link.

FIG. 4 is a detailed block diagram of the audiometer of the present invention.

FIG. 5 is a detailed block diagram of the programmable analog devices which produce the test tones.

FIG. 6 is a general flow diagram of the operating algorithm according to the audiometric method and system of the invention.

FIG. 7 is a detailed flow diagram of an initial test subroutine contained in block 84 of FIG. 6.

FIG. 9 is a more detailed flow diagram of a computational subroutine contained in block 85 of FIG. 5.

FIG. 10 is a more detailed flow diagram of a diagnosing subroutine contained in block 88 of FIG. 5.

DESCRIPTION OF THE INVENTION

Figure 8:
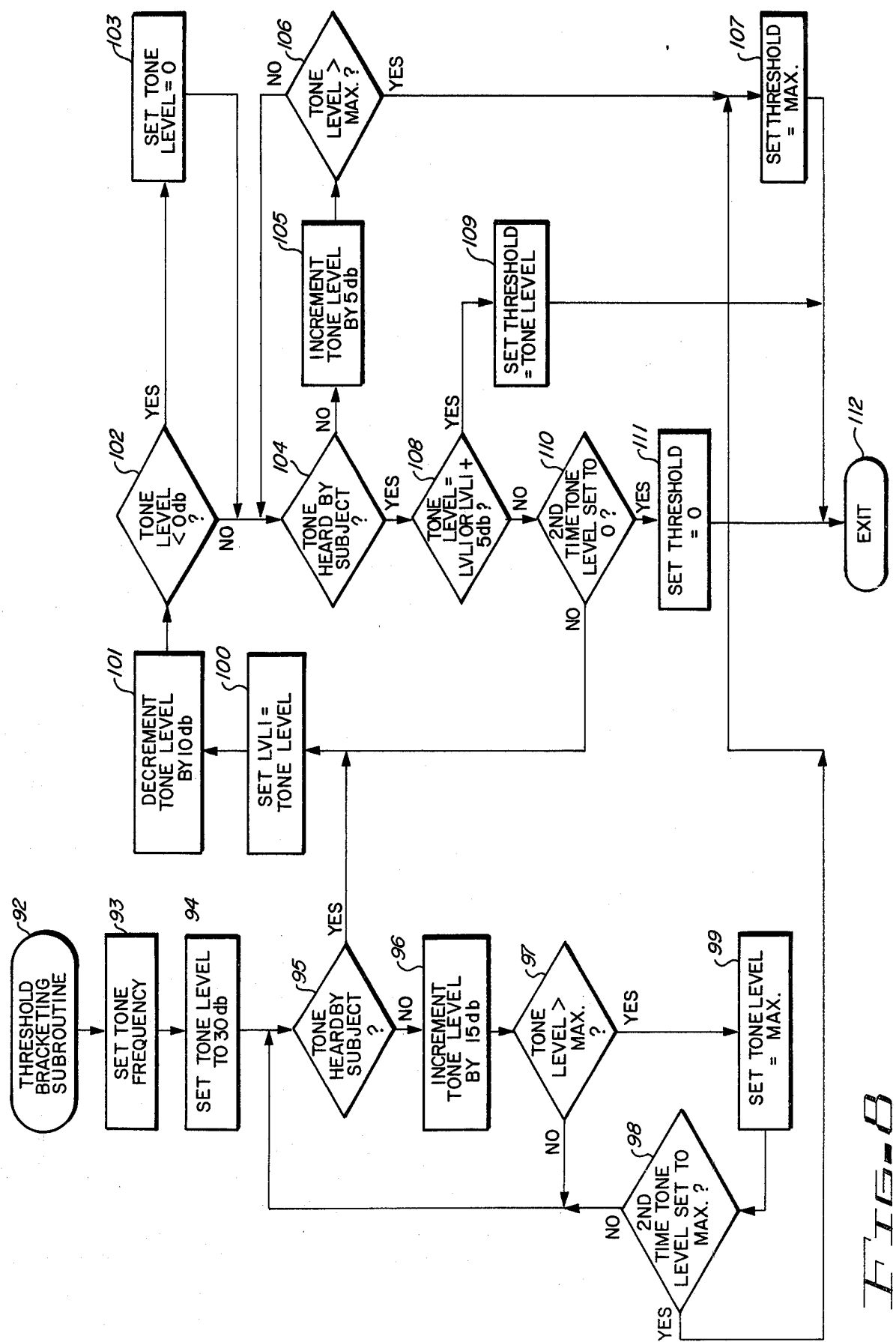
FIG. 8 is a detailed flow diagram of a threshold bracketing subroutine contained in block 84 of FIG. 5.

The audiometric system of the present invention greatly simplifies audiometric testing and recordkeeping by permitting a "local" audiometer to access a remote data processing system storing a large number of audiometric records to "fetch" a selected set of audiometric records corresponding to a selected group of subjects who are to be tested during a particular day. The subjects are tested in accordance with a threshold bracketing procedure. An essentially similar threshold bracketing procedure which can be used is described in detail in commonly assigned U.S. Pat. No. 3,974,335, filed on June 6, 1974 and issued Aug. 10, 1976, by this inventor, and incorporated herein by reference. The audiometric system utilizes the results of a current audiometric testing of a subject with the corresponding test results contained in the "fetched" audiometric records from prior testing of that subject to automatically compute certain audiometric parameters and identify any significant hearing threshold shifts for the subject. If a significant hearing threshold shift is detected, this fact is automatically signaled to an operator of the audiometric system. The audiometric system of the present invention further recommends subsequent action by means of a printed message. For example, the printed message may recommend that the subject be retested within one month to confirm the results of the present test. The audiometric system then prints as many complete "original" audiometric records as desired for the subject. Such "original copy" records greatly simplify the bookkeeping aspects of audiometric history record keeping and are legally admissable documents in potential liability litigation.

Figure 1B:
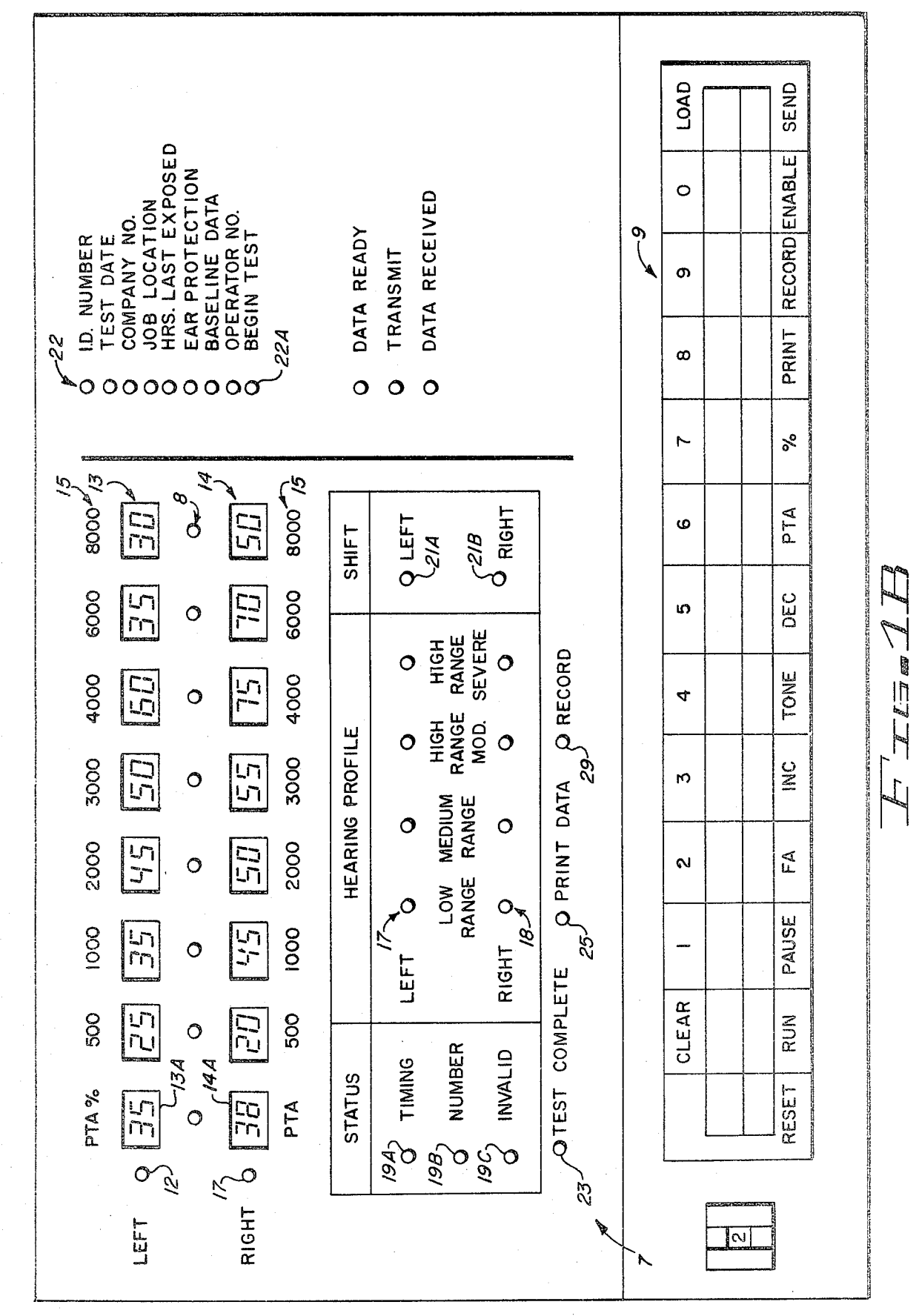

Referring now to the drawings, and particularly to FIGS. 1A and 1B, audiometric system 1 includes an audiometer 3 coupled by means of a cable to printer 5. Audiometer 3 includes a display 7, a keyboard 9, and a mode selection switch 11. Upon completion of audiometric testing of a patient or employee, audiometer 3, operating in accordance with a stored algorithm, causes printer 5 to print out a "hard copy" record 24 for the patient being tested, as subsequently explained.

The details of display 7 and keyboard 9 are shown in FIG. 1B. Display 7 includes two rows of display devices, generally designated by reference numerals 13 and 14 for displaying threshold levels for the left and right ears, respectively, of the test subject. The frequencies to which such threshold levels correspond are generally designated by reference numeral 15.

The pure tone averages (PTA) for the left and right ears of the test subject are displayed by display devices 13A and 14A, respectively, if key number 6 of keyboard 9 is depressed at the appropriate time, as subsequently explained. Display devices 13A and 14A display the percent binaural hearing impairment if key number 7 is depressed at the appropriate time. During execution of an algorithm implementing a modified version of the well-known Hughson-Westlake bracketing algorithm, the present frequency of testing is indicated by light emitting diodes generally designated by reference numerals 8, and the ear (left or right) being tested as indicated by one of light emitting diodes 12 and 17.

Pure tone averages are utilized to assess the degree of hearing impairment of the subject. The audiometer 3 automatically performs the pure tone average calculation by summing the threshold levels of each ear for frequencies such as 500, 1,000, and 2,000 Hertz and dividing the total by three. The percent binaural hearing impairment is determined by the AAOO criterion; the calculation is set forth hereinafter. A threshold shift calculation is automatically completed when the audiometer is provided with base line data either by keyboard or remotely from the remote data processing system. Light emitting diodes 23, 25 and 29, which are provided located adjacent the "test complete", "print data", and "record" labels, respectively, are illuminated to prompt the operator to initiate the print operation, the operation of recording the present test results, and the operation of updating the records of the present subject.

As the test progresses, display devices 13 and 14 sequentially light up until the entire audiogram of the patient being tested is displayed. Further, the pure tone average (PTA) or percent binaural impairment, depending upon whether key 6 or key 7 is depressed at an appropriate time, is displayed.

The "status" display section of display 7 includes light emitting diodes 19A, 19B and 19C positioned adjacent the words "timing", "number", and "invalid", respectively, to indicate whether the patient is properly responding to the test tones, or if the test is determined to be invalid by an initial test of the left ear at 1,000 Hertz, as subsequently explained. Should the test be invalid, an automatic printout message identifies the cause.

The "hearing profile" section of display 7 indicates, for both left and right ears of the subject, any significant hearing impairment for the low, medium and high frequency ranges and also indicates severe impairment for the high frequency range by means of the light emitting diodes generally designated by reference numerals 17 and 18. This display illuminates the presence of a hearing loss in the low, medium and high ranges in both ears if the thresholds exceed the levels shown below by five decibles:

| Range | Normal Maximum |
|---|---|
| low | 25dB |
| mid | 25dB |
| high moderate | 25dB |
| high severe | 55dB |

The "shift" section of display 7 indicates any significant threshold shift for either the left or right ear of the subject, as indicated by light emitting diodes 21A and 21B, respectively.

Display 7 includes an "operator prompting display section" including a plurality of light emitting diodes generally designated by reference numeral 22. The operating algorithm of audiometric system 1 causes light emitting diodes 22 to light up sequentially to prompt the operator to enter the indicated information into audiometer 3 by means of keyboard 9. When all required data has been entered, a red light emitting diode 22A immediately to the left of the words "BEGIN TEST" lights up.

FIG. 2 illustrates a typical "hearing test record" printout from printer 5. As can be seen from FIG. 2, the hearing test record printed by printer 5 contains a complete audiogram, computed audiometric parameters (pure tone average (PTA) and percent binaural hearing loss (PBHL)), and pertinent information relating to the test subject, including an I.D. number. If the test date, company number, job location, etc., are not contained in the audiometric records retrieved from the remote data processing system, they must be entered into audiometer 3 by means of keyboard 9 before audiometer 3 will perform audiometric testing of the subject. The presently measured thresholds for both the left and right ears are indicated at each of the frequencies indicated by reference numeral 15 in FIG. 1B. The base line data, subsequently defined, is also printed out for each ear. The pure tone average (PTA) and the percent binary hearing loss are printed out for each ear. The printed record indicates whether there is a threshold shift, and indicates when the patient should be retested. It also identifies the operator by name. At the bottom of FIG. 2, the two rows of unformatted numbers constitute the complete set of data which is subsequently transmitted to the remote data processing system 28.

The printout is obtained by simply pressing the PRINT key of keyboard 9 after the "test complete" indicator 23 of display 7 light ups. As many "hard copy" records as desired can be obtained at this point by simply repeatedly depressing the "print" key.

Referring to FIG. 3, a generalized block diagram of the audiometric system 10 is shown. Audiometric system 10 includes audiometric system 1 of FIG. 1A includes audiometer 3 and display 7. Printer 5 is connected by means of a cable to audiometer 3. Audiometer 3 is connected to a communications link 26 to a remote data processing system. Typically, communications link 26 is a telephone system communications link.

A detailed block diagram of complete system 10 of FIG. 3 is shown in FIG. 4. System 10 includes a microprocessor 30 having a sixteen bit address bus 32 and an eight bit bidirectional data bus 34 connected thereto. Read only memory (ROM) 35 has its data output terminals connected to data bus 34 and its address input terminals connected to address bus 32. Read only memory 35 stores the previously mentioned operating algorithm for audiometer 3. Random access memory (RAM) 36 has its data terminals connected to data bus 34 and its address terminals connected to address bus 32. Communications interface circuit 37, keyboard and associated keyboard encoder 9, mode switch 11, response device 40, programmable tone control circuitry 42, and display control circuitry 7 all include data terminals connected to data bus 34 and decoding circuitry having address inputs connected to address bus 32.

Random access memory 36 includes a scratch pad portion for storing intermediate calculation results and the like, and also includes a audiometric record storage section for storing complete audiometric records for fifty subjects, and is, of course, expandable if desired.

In the presently implemented embodiment of the invention, microprocessor 30 is a SC/MP microprocessor, manufactured by National Semiconductor, Inc. Read only memory 35 is organized as 8192 words by eight bits, and is implemented utilizing National Semiconductor 5204Q programmable read only memories. Random access memory 36 is implemented utilizing static MOS random access memory integrated circuit chips. 256 words by eight bits of random access memory 36 are utilized as a scratch pad, and 4,096 words by eight bits are utilized for audiometric record file storage. Suitable integrated circuit statis MOS random access memory chips are readily available from National Semiconductor, Intel, Motorola, Texas Instruments, and others.

Communications interface circuit 37 performs the function of parallel-to-serial conversion of data transmitted to the remote data processing system 28 and also performs the function of serial-to-parallel data conversion for serial data received from remote data processing system 28. It may be implemented utilizing various readily commercially available UARTS (universal asynchronous receiver transmitter) or asynchronous communications interface adaptors, such as the Motorola MC 6850.

Circuitry 26A includes a modem and acoustic coupler unit, such as the Omnitek model 701B, and can be readily provided by those skilled in the art.

The keyboard and associated encoder designated by reference numeral 9 can be readily implemented by those skilled in the art. Response device 40 can be a thumb activated switch held by the subject during testing. The subject simply depresses a thumb button (in accordance with prior instructions given to him by the test operator) when he hears a particular tone or pattern of tones. Alternatively, response device 40 can include a keyboard having a plurality of numbered keys. The subject is instructed to indicate how many test tones (of a predetermined frequency and intensity) he hears, and depresses the numbered key corresponding to the number of test tones that he hears.

Display 7 includes various readily available alphanumeric displays and display drivers.

Mode switch 11 is a multi-position switch whose functions are described in detail later.

Microprocessor 30 periodically accesses all of the elements shown in FIG. 4, in accordance with the stored operating algorithm, to perform the necessary information retrieval, calculating, data storage, keyboard interpretation, tone control, subject response, and printing control functions necessary for operation of audiometric system 10. Programmable tone control circuitry 42 generates the particular tones at predetermined frequencies and intensities in response to microprocessor 30 as required to obtain the complete audiograms for both ears of the subject being tested.

The major details of programmable tone control circuitry 42 are shown in FIG. 5. Programmable tone control circuitry 42 includes an oscillator 50, tone intensity control circuitry 52, and switch 44. Switch 44 simply controls whether the output of tone intensity control circuitry 52 is applied to left earphone 48 or right earphone 46 of a headset worn by the subject. Oscillator 50 is controlled by means of a programmable resistor array 54. Each of a plurality of resistors in array 54 is electrically connected to ground by means of a plurality of switching transistors 56 in response to control signals produced by decode circuitry 58. Decode circuitry 58 produces such control signals in response to a tone frequency control word received from microprocessor 30 via data bus 34. Decode circuitry 58 includes the Fairchild 9334 decoder integrated circuit as its main component. Timing signal CLK1 is applied to gate the control information from data bus 34 into decode circuitry 58 by means of conductor 60.

The width of each continuous burst of tone signals from oscillator 50 at a frequency determined by decode circuitry 58 and resistor array 54 is controlled by clock circuit 62. Clock circuit 62 responds to start tone signals applied to conductor 63 and stop tone signals applied to 64 to produce the signals necessary to start and stop each tone burst. The start tone and the stop tone signals are produced in response to microprocessor 30.

The intensities of the test tones are controlled by tone intensity control circuitry 52, which includes a plurality of programmable attenuators. The programmable attenuators are programmable in response to resistors of a resistor array 66 which are respectively coupled to ground by means of a plurality of switching transistors 68. Switching transistors 68 respond to decode circuitry 70, which receives a tone intensity control word from microprocessor 30 via data bus 34. The tone intensity control word is gated into decode circuitry 70 by means of a control signal CLK2, which is applied to conductor 72. Decode circuitry 70 includes a Fairchild 9334 decoder integrated circuit as its main component, and is readily implementable by those skilled in the art.

The operation of audiometer 3 of FIG. 1A is as follows. First, mode selector switch 11 is set to determine the desired operating mode. Five different modes may be selected, which respectively effect (1) execution of an automatic threshold identification subroutine, hereinafter referred to as a "bracketing" subroutine, (2) execution of a "slow" automatic threshold identification subroutine for testing slowly responding patients, (3) execution of a "manually controlled" threshold identification subroutine, (4) execution of a threshold "counting" subroutine requiring the subject to depress a multiple-key hand held response keyboard (see response device 40 in FIG. 4) indicating the number of randomized test tones heard, (5) execution of a threshold "counting" subroutine requiring a slow responding test subject to indicate the number of test tones heard, and (6) execution of a subroutine causing audiometer 3 to interface with a remote data processing system 28 of FIG. 2 to fetch or store audiometric records.

During the execution of the above automatic threshold identification subroutines, the previously mentioned modified Hughson-Westlake bracketing technique is employed, wherein the test tones transmitted to the earphones worn by the subject begin at a sound level of thirty decibels. The "bracketing" subroutine decrements the sound level by ten decibels if the test subject indicates that he hears the thirty decibel level, and awaits a response by the subject. If the subject does not respond, the subroutine then increments the sound level by five decibels. If the test subject indicates (by means of response device 40) that he hears the most recent test tone the intensity is again decremented by ten decibels. This procedure is continued, in order to "bracket" the threshold level of the test subject at a particular frequency. If, at a particular frequency, the subject does not hear the initial test tone at the thirty decibel level, the bracketing subroutine increases the sound level in fifteen decibel steps until the subject responds.

During execution of the bracketing subroutine, a randomized number of tones (at the predetermined decibel levels) are presented to the subject under test in order to increase the validity of the test results.

The manual test subroutine permits the operator to manually control the test tone levels and frequencies. The test tone level can be increased by five decibels by depressing the INC key of keyboard 9 and can decrease the test tone level by five decibels by depressing the DEC key. When the TONE key is depressed, a series of three pulse tones at the selected level and frequency are produced. The frequency can be manually advanced by depressing the FA key.

It should be noted that keyboard 9 is a dual purpose keyboard which is utilized for both data entry and test control. All of the keys except the RESET key perform two functions, as indicated by the upper and lower labels adjacent each key. Hereinafter the various keys are referred to by their function under discussion. The RESET key is utilized to clear the audiometer prior to entering data for a new test subject. The CLEAR key enables the test operator to correct an entry. The LOAD key is utilized to store information into the random access memory 36 of FIG. 4. The RUN key is depressed to initiate execution of the hearing test algorithm by microprocessor 30. The PAUSE key can be utilized to temporarily interrupt execution of an automatic testing sequence. (This may be necessary to instruct a test subject who fails to understand how to respond to the test tones.) Execution of the automatic testing sequence may subsequently be resumed by depressing the PAUSE key a second time. The FA key may be utilized during the manual testing mode to advance to the next frequency (indicated by reference numeral 15 in FIG. 1B). The INC key is utilized during the manual test mode to increment the intensity of the test tone by five decibels. The amplitude of the presented tone is automatically indicated on the display panel. When the TONE key is depressed (in the manual testing mode of operation), audiometer 3 presents a series of three test tone pulses to the subject. The DEC key can be depressed by the operator to decrease the intensity of the test tone by five decibels during the manual testing mode. After completion of the autiometric testing microprocessor 30 automatically calculates the pure tone average, which is displayed in the indicated location (13A and 14A of FIG. 1B) on display 7 when the PTA key is depressed. Depressing the % key causes display of the percent binaural hearing loss. The PRINT key causes printer 5 to print the complete hearing test record of the present test subject, including relevant instrument constants, audiometer make, model, serial number, calibration, and operator number. The RECORD key is utilized to enter the present test results and computation results into the random access memory 36. The ENABLE and SEND keys are utilized in data transmission, as subsequently explained. The key designated "PAUSE" can also be used to effect the "log on" operation, subsequently described. At appropriate stages of operation the keys of keyboard 9 can also be used to enter numerical data, as indicated by the labels 1-9 and 0.

As an example of operation, assume that a particular group of subjects are to be tested on a certain day. At the beginning of that day the operator selects the data transmission mode, hereinafter referred to as "mode 9", by means of mode selector switch 11. In mode 9, the operating algorithm permits the operator to monitor the contents of random access memory 36 and/or perform transfers of data to and from remote data processing system 28. The operator causes the algorithm to enter mode 9 by depressing the RESET and the RUN keys.

The various keys of keyboard 9 perform the following functions when the algorithm is operating in mode 9.

Key "1"—a coded command is sent to remote data processing system 28 to "log-on" and obtain access to the audiometric records stored therein.

Key "2"—causes audiometer 3 to "log-off" from remote data processing system 28.

Key "3"—aborts audiometer-to-remote data processing system communication.

Key "4"—initiates execution of a program effecting receiving and storing of new test results into random access memory 36.

Key "5"—executes a stored subroutine which causes entered identification numbers to be transmitted to remote data processing system 28, requesting that remote processing system 28 search its files and transmit corresponding audiometric records back to audiometer 3.

Key "6"—enables entry of identification numbers entered via keyboard 9 into microprocessor 30 for subsequent transmission to remote data processing system 28.

Key "7"—undefined.

Key "8"—causes a print-out of a portion of random access memory 36 containing audiometric records.

Key "9"—undefined.

Key "0"—causes a print-out of an index of the contents of random access memory 36, indicating the amount of memory space available for new test records, the number of stored test records containing identification numbers only, the number of stored records for presently untested subjects, and the number of subjects yet to be tested.

"CLEAR" key—instructs the audiometer to stop its current acitivty when communicating with remote data processing system 28.

"SEND" key—instructs microprocessor 30 to send a line of code during the "log-on" procedure.

To continue the above example, once the algorithm is in mode 9, the operator can depress Key "0" to display the current status of random access memory 36. The operator then depresses the RUN key and Key "6", and then enters an identification number via keyboard 9.

Next, the operator depresses the LOAD key. The operator depresses the RESET key after all indentification numbers have been loaded. At this point, the operator may depress key "0" to obtain the updated status of random access memory 36. Next, the operator "logs-on" to remote data processing system 28 by depressing key "0".

Audiometer 3 then sends the loaded identification numbers to remote data processing system 28, which executes a program to fetch the requested audiometric records and transmit them back to audiometer 3. If an erroneous identification number has been entered into keyboard 9, the operating algorithm causes that number to be erased from random access memory 36. At this point, the operator can again depress Key "0" to obtain the most recent status of random access memory 36.

The audiometer may, at this point, perform audiometric testing in accordance with the subsequently explained bracketing subroutine.

Should the operator attempt to retest a subject who has already been tested, a message will be automatically printed out indicating that the subject has already been tested.

After all subjects have been tested, the operator again causes the algorithm to enter mode 9, and depresses Key "1" to "log-on" to remote data processing system 28. Microcomputer 10 then causes execution of a subroutine which causes the audiometer 3 to transmit the updated audiometric records or new audiometric records of subjects tested that day to remote data processing system 26, and "logs off" by depressing key "2". (It should be noted that at any time during operation in the data transmission mode, the operator may return the audiometric system to another test mode by changing mode selection switch 11 to the desired mode and depressing the RESET key. At this point the operator may obtain a "printout" of a numerical data stream representing data stored in random access memory 36 by depressing the PRINT key.

To summarize, in order to obtain "base line" data (usually the most recent prior valid and confirmed set of threshold levels for the subject) from remote computer 28, the operator must enter the identification numbers of individuals to be tested. The operator then depresses key "6". The one of light emitting diodes 22 corresponding to the subject's identification number is illuminated. The identification numbers are then loaded into the system including microprocessor 30 and random access memory 36 by depressing the LOAD key. When all desired identification numbers have been loaded, the operator depresses the RESET key to display an updated random access memory status. If the portion of random access memory dedicated to storing audiometric records is completely filled, "F's" appear in display 14.

The operator depresses key "1" (the PAUSE key) in order to "log on" and send the required command to remote data processing system 28 to obtain access to the audiometric data files corresponding to the previously entered identification numbers. Next, the operator depresses key "5" to cause execution of the subroutine which enables the previously entered identification numbers to be sent to remote data processing system 28. Upon receipt of such identification numbers, remote data processing system 28 checks its files for corresponding base line data and sends the base line data to microprocessor 30, which causes it to be stored in random access memory 36. Upon completion of fetching the required audiometric data files from the remote data processing system 28, the test operator "logs off" by depressing Key "2". During the day, the test operator tests the various subjects, as subsequently explained. At the end of the day the test operator transmits the newly obtained test threshold levels for the tested subjects to remote data processing system 28 by depressing key "1" and then depressing key "4" to execute a subroutine that causes the stored test results to be transmitted to remote data processing system 28. Upon completion of this operation, the operator depresses key "2" to "log off".

Operation of audiometer 3 after the required audiometric files have been fetched from remote data processing system 28 is explained next. After the operator has completed such fetching by means of the previous operation, the operating algorithm causes the light emitting diodes 22 in the operator prompting section of display 7 to prompt the operator to key in required numerical data. First, the "I.D. number" light emitting diode illuminates, prompting the operator to type in the identification number (e.g. the social security number) of the next test subject. The number typed in is displayed by means of display device 13 of FIG. 1B. An incorrectly entered number may be erased by depressing the CLEAR key. When the information is correctly entered, it is loaded into random access memory 36 by depressing the LOAD key. Similarly, the test date, company number, job location, number of hours the subject was last exposed to noise, ear protection data, base line data, and operator number are all entered by means of keyboard 9 and loaded into random access memory 36 if they are not already present in random access memory 36 as part of the audiometric records previously fetched from remote data processing system 28. When all necessary information is present in random access memory 36, the one of light emitting diodes 22 adjacent the "begin test" label indicator is illuminated. The test subject is instructed to momentarily depress a button of the hand-held response device 40 as soon as any sequence of two or three random beeping tones ceases to beep, if the automatic test modes are utilized.

Once the subject's earphones are in place, execution of the automated test subroutine is initiated by the operator by depressing the RUN key. An initial validity check test is performed by running a sample test at 1,000 Hertz in the left ear of the subject. A retest is then performed to ensure that the same results are obtained, within a five decibel error limit. If the retest results are different from the initial results by more than five decibels, printer 5 will be caused to automatically print out the message "1,000 HZ AUTO VALUE FAILURE". At this time, it is necessary for the operator to temporarily suspend testing by pressing the PAUSE key. Further instruction of the subject is probably required to ensure that he understands how to respond to the test tones. Testing is resumed by again depressing the PAUSE key of keyboard 9.

During the automatic testing operation, the "timing" display indicator (light emitting diode 19A of FIG. 1B) will momentarily illuminate if the subject responds by depressing the response button while a test tone is being presented. An algorithm causes audiometer 3 to disregard such a response, and delivers the tone pattern again at the same amplitude and frequency. The algorithm causes the testing to cease automatically if three or more such timing errors are encountered at a given test tone frequency. In this case, the test operator should determine whether the subject is merely guessing or has misunderstood the test instructions.

If the test is being performed in the one of the previously mentioned "tone-counting" operating modes, the "number" display indicator 19B (FIG. 1B) illuminates if the test subject depresses one of the above-mentioned numbered buttons which fails to correspond to the randomized number of tones presented. This response is treated as if no response had been given, and the next group of random tones at the same frequency is presented at the next higher intensity level.

The "invalid" indicator 19C (FIG. 1B) illuminates when the subject simultaneously depresses more than one response button more than three consecutive times.

The operator can retest the subject in the same mode by depressing the LOAD key and then depressing the RUN key. Alternatively, the operator can retest in a different test mode by first selecting a new test mode by means of mode selector switch 11, and then consecutively depressing the LOAD and RUN keys. This is accomplished without loss of current identification data for the present test subject.

Should the operator elect to utilize the manual test mode, the FA, INC, DEC, and TONE keys are utilized as previously indicated.

Once the testing of the present subject is complete at all frequencies, the "test complete" indicator 23 illuminates. The PTA and percent keys can then be depressed to display the results of pure tone average and percent binaural impairment computations.

Upon completion of a test in the automatic mode, the hearing test record 24 is automatically printed by printer 5. If base line information was entered into random access memory 36 either by means of keyboard 9 or was received from remote data processing system 28, an automatic threshold shift calculation is performed. Any significant shift in threshold level is indicated by light emitting diodes 21A or 21B, and is printed out along with the other audiometric information in hearing test record 24. Additional "hard copy" records of the test results for the subject can be obtained by momentarily depressing the PRINT key.

The test results and computation results are then loaded into random access memory 36 by depressing the RECORD key. The operator then depresses the RESET button to prepare audiometric testing system 1 to test the next test subject.

The basic operations involved in operating the audiometric system of FIGS. 3 and 4 are set forth in the flow diagram of FIG. 6. Referring now to FIG. 6, the algorithm begins operation at label 74, and initializes various storage elements in the system, as indicated by 75. The algorithm then causes microprocessor 30 to read the setting of the mode select switch 11, as indicated by 76. If the mode select switch 11 is in "mode 9" (the mode for monitoring the contents of random access memory 36 or communicating with remote data processing 28), the operating algorithm enters decision block 78 to determine whether the operator wishes to transmit audiometric records presently contained in random access memory 36 to remote data processing system 28 or fetch audiometric records from remote data processing system 28 and store them in random access memory 36. (The operation of monitoring the contents of random access memory 136 was previously described, and is not further set forth in FIG. 6.)

If the operator wishes to fetch audiometric records from the remote data processing system (DPS), the algorithm causes microprocessor 30 to transmit identification numbers corresponding to audiometric records stored in remote data processing system 28 and transmit such identification numbers to remote data processing system 28, as indicated by blocks 79 and 80. The remote data processing system 28 then sends the requested audiometric records to microprocessor 30, and the algorithm of FIG. 6 causes the audiometric records fetched to be loaded into random access memory 36. The algorithm is then reentered at "start" label 74.

If the operator changes the setting of mode select switch 11, the algorithm enters the new mode, as indicated by block 83. The algorithm then enters block 84 and effects performance of the required audiometric tests in accordance with the selected mode. The flow diagrams of FIGS. 7 and 8 set forth subroutines which are executed to perform such audiometric tests if one of the automatic testing modes is selected.

Referring now to FIG. 7, the algorithm enters the previously described 1,000 Hertz trial test subroutine at label 124, and causes the left ear of the test subject to be tested at 1,000 Hertz, as indicated by block 125. The test performed in accordance with block 125 is substantially the same test as subsequently described with respect to FIG. 8. After the left ear test has been performed, the trial test subroutine causes both ears of the subject to be tested at 500 Hertz, in accordance with the details of FIG. 8, as indicated in block 126 of FIG. 7. The trial test algorithm then retests the left ear at 1,000 Hertz, as indicated at block 127. The algorithm then enters decision block 128 to compare the first test threshold at 1,000 Hertz with the retest threshold measured at 1,000 Hertz. If the two foregoing thresholds are within ±5 decibels of each other, the trial test is deemed valid, and the trail test subroutine is exited at label 130. If the foregoing two threshold levels are not within ±5 decibels, an error message is caused to be printed, as indicated at block 131. The algorithm then waits for the operator to depress PAUSE key to exit at label 130 or the LOAD key to re-enter at label 124.

When the algorithm exits the trial test subroutine of FIG. 7 at label 130, it enters threshold bracketing subroutine of FIG. 8 at label 92.

Referring now to FIG. 8, the automatic tone generation or bracketing subroutine set forth in FIG. 8 sets the tone frequency at one of the various frequencies indicated in FIG. 1B, depending upon how far through the testing procedure the algorithm has progressed. For the selected frequency, the tone level is set to thirty decibels, as indicated at block 94. The term "tone level", as used in the following discussion, refers to both the intensity of the test tone produced and to a "test tone intensity logic variable", the value of which is utilized by microprocessor 30 to determine the intensity of the test tone currently presented to the subject.

The algorithm then enters decision block 95 to determine from the subject's response (communicated via the response button or response keyboard) whether the subject heard the previously applied test tone pattern. If the subject did not hear the previous test tone pattern, the tone level is incremented by fifteen decibels, as indicated at block 96. If the incremented tone level is not greater than a predetermined maximum value (which can be approximately 95 decibels) the algorithm reenters decision block 95. The algorithm keeps incrementing the tone level by fifteen decibels until the predetermined maximum level is reached or the subject indicates that he hears the test tone pattern presented to him. If the tone level reaches the maximum value, as indicated at block 99 and the subject still does not hear the test tone presented to him, the algorithm sets the threshold corresponding to the selected frequency to the maximum level and exits from the automatic tone generation subroutine, as indicated by decision block 98, block 107, and label 112.

If the subject hears the applied test tone, the algorithm enters block 100 from decision block 95, and sets a logic variable called LVL1 equal to that tone level. The tone level is then decremented by ten decibels, as indicated at block 101. If the tone level is not less than zero decibels, the algorithm enters decision block 104. If the tone level is less than zero decibels, the algorithm sets tone level equal to zero and enters decision block 103. If the resulting test tone is not heard by the subject, the tone level is incremented by five decibels. If the incremented tone level is greater than the above-mentioned maximum level, the threshold is set to the maximum level and the automatic tone generation subroutine is exited, as indicated by decision block 106, block 107, and label 112. If the incremented tone level is not greater than the maximum, the algorithm reenters decision block 104.

If the subject then hears the applied test tone, the algorithm enters decision block 108 and determines if the tone level is equal to LVL1 or LVL1+5 decibels. If the tone level is within five decibels of LVL1, the algorithm sets the threshold equal to the tone level and exits, as indicated in blocks 108 and 109.

If the tone level has been set to zero for a second time as the algorithm passes through block 103, the threshold is set to zero, as indicated by blocks 110 and 111. If not, the algorithm reenters block 100 from decision block 108, as indicated by decision block 110.

Referring again to FIG. 6, after the audiometric tests have been performed and the threshold levels have been determined for all the frequencies indicated in FIG. 1B, the pure tone average (PTA) and the percent binaural hearing loss (PBHL) are computed, as indicated at block 85. The flow diagram of FIG. 9 illustrates the basic steps of the subroutine of the operating algorithm for computing PTA and PBHL.

Referring to FIG. 9, the computation subroutine is entered at label 115. The pure tone average is then computed on the basis of the previously measured threshold levels, as indicated by block 116. For each ear, the pure tone average is computed by summing the thresholds at 500, 1,000, and 2,000 Hertz and dividing that sum by three.

The algorithm then computes the percent binaural hearing loss in accordance with AAOO standards, as indicated at block 117. The computation is made in accordance with the formula $$\frac{PTA \text{ (larger)} - 25 + 5 (PTA \text{ (smaller)} - 25)}{6},$$

where PTA(larger) and PTA(smaller) are the larger and smaller of the two previously computed pure tone averages.

Next, if prior records for the subject have been received from remote data processing system 28 or entered by means of keyboard 9, the algorithm computes any threshold shift for each ear. If the threshold shift for a particular ear exceeds ten decibels, a logical variable TS is set to a logical one, as indicated at 119. Next, the algorithm computes the hearing profile information to be displayed in section 18 of display 7 in FIG. 1A. For each ear, a logic variable LR is set to a one if the threshold for the ear at 500 Hertz is greater than or equal to twenty-five decibels, as indicated in block 120. For each ear, a logic variable MR is set to a logical "one" if the threshold level for that ear exceeds or is equal to twenty-five decibels for 1,000, 2,000 or 3,000 Hertz, as indicated at block 121. For each ear, a logic variable HRM (high range medium) is set to a logical "one" if a threshold level for that ear exceeds twenty-five decibels at 4,000 or 6,000 Hertz, as indicated at block 122. For each year, a logic variable HRS (high range severe) is set to a logical "one" if the threshold level for that ear exceeds sixty decibels at 4,000 or 6,000 Hertz. The algorithm then exits the computation subroutine of FIG. 9.

Referring again to FIG. 6, the operating algorithm tests the previously mentioned logic variables to cause illumination of the appropriate ones of the light emitting diodes shown in FIGS. 1A and 1B. The algorithm then enters block 88 and performs a diagnosis, details of which are shown in the flow diagram of FIG. 10.

Referring now to FIG. 10, a diagnosis subroutine is entered at label 137. A logical variable called YM (year/month) is set to a logical zero, as indicated at 138. The algorithm then enters decision block 139 to determine whether the present test is the first time that the subject has been tested. If so, no previous audiometric records exist for the subject, and the algorithm sets YM equal to a logical "one" and exits from the diagnosis subroutine, as indicated at 140 and 143. If the present test is not the initial test of the subject, the diagnosis subroutine enters decision block 141 and tests the TS variables for each ear to determine if there was a significant threshold shift. If there was a significant threshold shift, the diagnosis subroutine is exited at 143. If there was no significant threshold shift in either ear, the algorithm sets YM equal to a logical "1" and exits. As subsequently explained, if YM is set to a logical "zero", a diagnostic message is printed recommending retesting in one month to confirm the presently detected threshold shift. If YM is equal to a "one", a diagnostic message recommending retesting in one year is printed out. After the diagnosis has been performed, the algorithm of FIG. 6 prints the hearing test record, as indicated at block 89, in accordance with the details shown in FIG. 11.

Figure 11:
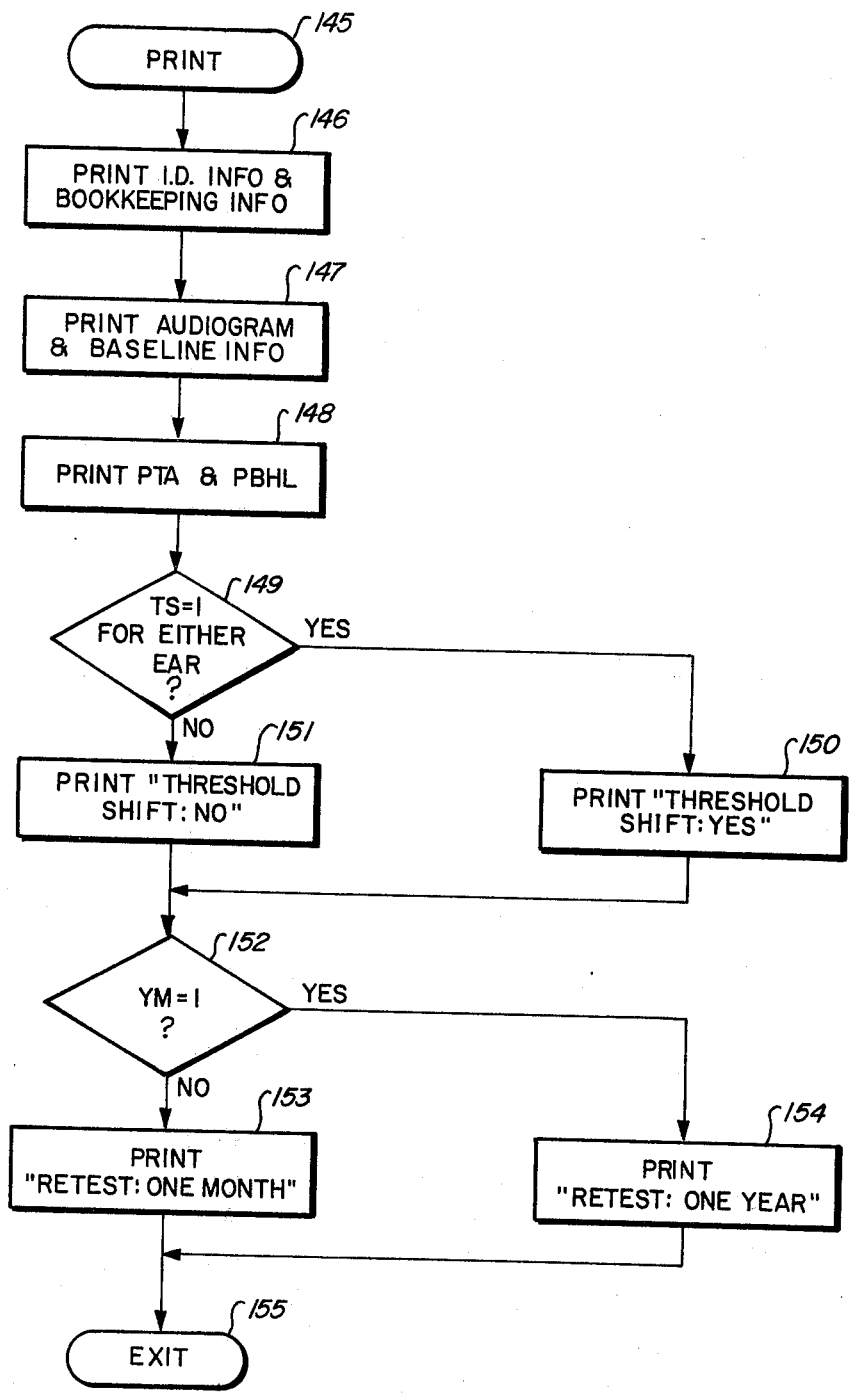
FIG. 11 is a more detailed flow diagram of a print control subroutine contained in block 89 of FIG. 5.

Referring to FIG. 11, the printing subroutine is entered at label 145, and identifying information, bookkeeping information, the base line information in the memory, and the results of the PTA and PBHL calculations are printed out, as indicated by blocks 146, 147, and 148.

The print subroutine then tests the TS flags for each ear, as indicated by decision block 149, and prints the messages indicated in blocks 150 and 151 if TS is a "one" or a "zero", respectively, for either ear. As previously stated, the printer can print out the record of subject's complete hearing test results, including significant threshold shifts. The print subroutine then tests the YM flag, as indicated at decision block 152, and accordingly prints the messages indicated in blocks 153 and 154, and exits at label 155.

Returning to FIG. 6, the operating algorithm finally stores the current test results and computations in random access memory 36, upon detecting of a depressing of the record button key by the operator.

While the principles of the invention have now been made clear in an illustrative embodiment, there will be immediately obvious to those skilled in the art many modifications of structure, arrangement, proportions, element, materials, and components, used in the practice of the invention which are particlarly adapted for specific environments and operating requirements without departing from those principles.

I claim:

1. A method for audiometric testing of a first person by utilizing an audiometer located at the site of audiometric testing of the first person, the audiometer including
   (i) a first processor,
   (ii) a first memory included in the first processor,
   (iii) coupling means for optionally operatively coupling, at the option of an operator, the audiometer to a second processor, the second processor being a remote processor including a second memory capable of storing a plurality of prior threshold levels previously obtained by past audiomeric testing of the first person, said audiometer being operable, with no modification thereto, to effect said audiometric testing with or without being operatively coupled to the second processor, said coupling means including mode selection means for enabling the operator to select either a mode of operation of said audiometer wherein said audiometer is operatively coupled to a second processor or a mode of operation wherein said audiometer is not operatively coupled to the second processor,
   (iv) a printer coupled to the first processor, said method comprising the steps of:
   (a) manually entering said plurality of prior threshold levels into the audiometer, if the audiometer is not operatively connected by the coupling means to the second processor (of if) and said plurality of prior threshold levels is not contained in the second memory, the audiometer including keyboard means coupled to the first processor for manual entry of audiometric information into the audiometer;
   (b) utilizing the first processor to effect transfer of said plurality of prior threshold levels from the keyboard means to the first memory if the audiometer is not operatively coupled to the second processor;
   (c) utilizing the first processor to access the second processor via the coupling means to request the second processor to fetch said plurality of prior threshold levels from the second memory if the audiometer is coupled by the coupling means to the second processor;
   (d) utilizing the second processor to fetch said plurality of prior threshold levels from the second memory and to transmit the plurality of prior threshold levels to the first processor via the coupling means in response to said request and then operatively decoupling the second processor from the audiometer;
   (e) utilizing the first processor to digitally control selection of test tone frequencies and test tone intensities in accordance with a theshold bracketing subroutine stored in the first memory for execution by the first processor to determine a plurality of present threshold levels of the first person at the selected test tone frequencies, respectively;
   (f) utilizing the first processor to temporarily store said plurality of present threshold levels;

(g) utilizing the first processor to compute a threshold shift which has occurred in the first person since said previous audiometric testing; and (h) utilizing the first processor to effect printing of information indicative of whether said threshold shift is significant.

2. An audiometer comprising in combination:

(a) a first processor including a first memory;

(b) coupling means for optionally coupling and decoupling said audiometer to a second processor having a second memory capable of storing a plurality of prior threshold levels obtained by past teaching of a first person to allow the audiometer to be operated, without physical modification thereto, either with or without accessing the second computer to fetch prior threshold levels of the first person;

(c) keyboard means responsive to said first processor for effecting manual entry of said plurality of prior threshold levels if said plurality of prior threshold levels are not stored in said second memory and said audiometer is not operatively coupled by said coupling means to said second processor;

(d) control means responsive to said first processor for digitally controlling selection of test tone frequencies and test tone intensities in accordance with a threshold bracketing subroutine stored in said first memory to effect determining a plurality of present threshold levels of the first person at a plurality of the selected test tone frequencies, respectively, said first processor effecting temporary storing of said plurality of said present threshold levels in said first memory, said first processor also effecting computing of a threshold shift which has occurred since the past testing of the first person by averaging the differences between respective corresponding ones of said plurality of present threshold levels and said plurality of prior threshold levels; and (e) printing means responsive to said first processor for printing information indicative of whether said threshold shift is significant.

3. The method of claim 1 wherein step (e) includes utilizing the first processor to produce a pattern having a substantially randomized number of test tones of a particular test tone frequency, said method including utilizing the first processor to effect indicating of a mis-test if the first person responds to said pattern before said pattern is completed.

4. The method of claim 3 further including the step of requiring the first person to correctly indicate the number of test tones heard by the first person in said pattern and means for indicating a mis-test if the first person does not correctly indicate said number of test tones.

5. The audiometer of claim 2 further including means for producing a pattern including a substantially randomized number of test tones of a particular frequency and a particular intensity and means for indicating a mis-test if the first person responds to said pattern before said pattern is completed.

6. The audiometer of claim 5 further including response means for receiving a manual entry of the number of test tones in said pattern heard by the first person and means for indicating a mis-test if a number different than the true number of test tones in said pattern is entered into said response means.

7. The audiometer of claim 6 further including manual means for allowing manual incrementing and/or decrementing of the test tone frequencies and intensities.

8. The method of claim 1 including utilizing said first processor to effect displaying said plurality of present threshold levels and said average threshold shift and printing said plurality of present threshold levels.

9. The method of claim 1 including the step of utilizing said processor to effect transmitting said present threshold levels determined in step (g) to said secondary memory to update stored audiometric records of said first person.

10. The method of claim 1 including the steps of manually entering an identification number of said first person into said audiometer by means of the keyboard means and utilizing the first processor to effect transmitting said identification number to said second processor to identify audiometric records of said first person stored in the second memory.

11. The method of claim 1 including the steps of entering a plurality of identification numbers of a plurality of persons, respectively, into said audiometer and utilizing the first processor to effect transmitting said plurality of identification numbers to the second processor to identify audiometric records of said plurality of persons, utilizing the second processor to effect transmitting said audiometric records from the second processor to said audiometric system, utilizing the first processor to effect storing said audiometric records of said plurality of persons in the first memory, and individually testing said plurality of persons in accordance with steps (e) through (h).

12. The method of claim 11 further including the step of automatically instructing a test operator to enter information missing from said audiometric records of said first person stored in the first memory.

13. The method of claim 1 further including utilizing the first processor to effect computing a binaural hearing impairment perameter for said first person.

14. The method of claim 1 wherein said threshold bracketing subroutine implements a modified Hughson-Westlake threshold bracketing method.

15. The method of claim 8 further including the step of printing another copy containing the same information printed in accordance with claim 8 in response to a keyboard request by a test operator.

16. The audiometer of claim 2 further including:

(a) first means responsive to said first processor for producing a first test tone signal having a frequency determined by a first data word from said first processor;

(b) second means responsive to said first processor and said first test tone signal for producing a second test tone signal having the frequency of said first test tone signal and an intensity determined by a second data word from said first processor.

17. The audiometer of claim 16 further including third means responsive to said first processor for controlling the duration of said first test tone signal in response to control information from said first processor.

18. The audiometer of claim 2 including means for displaying said stored present threshold levels and said average threshold shift.

19. The audiometer of claim 2 further including means for transmitting said present threshold levels to said second memory to update audiometric records of said first person.

20. The method of claim 1 further including the step of automatically notifying an operator of said audiometer if said average threshold shift exceeds a predetermined value.

21. The method of claim 1 including the steps of retrieving said plurality of prior threshold levels from audiometric records of said first person prior to said entering said prior threshold levels into said audiometer by means of the keyboard means.

22. A method for audiometric testing of a first person by utilizing an audiometer located at the site of audiometric testing of the first person, the audiometer including (i) a first processor,
(ii) a first memory included in the first processor,
(iii) coupling means for optionally operatively coupling, at the option of an operator, the audiometer to a second processor, the second processor being a remote processor including a second memory capable of storing a plurality of prior threshold levels previously obtained by past audiometric testing of the first person, said audiometer being operable, with no modification thereto, to effect said audiometric testing with or without being operatively coupled to the second processor, said coupling means including mode selection means for enabling the operator to select either a mode of operation of said audiometer wherein said audiometer is operatively coupled to the second processor or a mode of operation wherein said audiometer is not operatively coupled to the second processor,
(iv) a printer coupled to the first processor, said method comprising the steps of:
(a) manually entering said plurality of prior threshold levels into the audiometer, if the audiometer is not operatively connected by the coupling means to the second processor and said plurality of prior threshold levels is not contained in the second memory, the audiometer including keyboard means coupled to the first processor for manual entry of audiometric information into the audiometer;
(b) utilizing the first processor to effect transfer of said plurality of prior threshold levels from the keyboard means to the first memory if the audiometer is not operatively coupled to the second processor;
(c) utilizing the first processor to access the second processor via the coupling means to request the second processor to fetch said plurality of prior threshold levels from the second memory if the audiometer is coupled by the coupling means to the second processor;
(d) utilizing the second processor to fetch said plurality of prior threshold levels from the second memory and to transmit the plurality of prior threshold levels to the first processor via the coupling means in response to said request and then operatively decoupling the second processor from the audiometer;
(e) utilizing the first processor to digitally control selection of test tone frequencies and test tone intensities in accordance with a threshold bracketing subroutine stored in the first memory for execution by the first processor to determine a plurality of present threshold levels of the first person at the selected test tone frequencies, respectively;
(f) utilizing the first processor to temporarily store said plurality of present threshold levels;
(g) utilizing the first processor to compute a threshold shift which has occurred in the first person since said previous audiometric testing; and
(h) utilizing the first processor to effect printing of said threshold shift by the printer.

23. An audiometer comprising in combination:
(a) a first processor including a first memory;
(b) coupling means for optionally coupling and decoupling said audiometer to a second processor having a second memory capable of storing a plurality of prior threshold levels obtained by past testing of a first person to allow the audiometer to be operated, without modification, either with or without accessing the second computer to fetch prior threshold levels of the first person;
(c) keyboard means responsive to said first processor for effecting manual entry of said plurality of prior threshold levels if said plurality of prior threshold levels are not stored in said second memory and said audiometer is not operatively coupled by said coupling means to said second processor;
(d) conrol means responsive to said first processor for digitally controlling selection of test tone frequencies and test tone intensities in accordance with a threshold bracketing subroutine stored in said first memory to effect determining a plurality of present threshold levels of the first person at a plurality of the selected test tone frequencies, respectively, said first processor effecting temporary storing of said plurality of said present threshold levels in said first memory, said first processor also effecting computing of a threshold shift which has occurred since the past testing of the first person by averaging the differences between respective corresponding ones of said plurality of present threshold levels and said plurality of prior threshold levels; and
(e) printing means responsive to said first processor for printing said threshold shift.

* * * * *